United States Patent [19]
Jumppanen et al.

[11] Patent Number: 5,939,565
[45] Date of Patent: Aug. 17, 1999

[54] RECOVERY OF γ-PYRONES

[75] Inventors: Juho Hermanni Jumppanen; Anu Ilona Ennelin, both of Espoo; Andrei Novomirovich Miasnikov, Kantvik, all of Finland

[73] Assignee: Cultor Food Science, Inc., Ardsley, N.Y.

[21] Appl. No.: 08/963,341

[22] Filed: Nov. 3, 1997

[51] Int. Cl.$^6$ .................................................. C07D 309/32
[52] U.S. Cl. ............................................................ 549/418
[58] Field of Search ............................................ 549/418

[56] References Cited

U.S. PATENT DOCUMENTS

| | | | |
|---|---|---|---|
| 3,130,204 | 4/1964 | Tate et al. | 260/345.5 |
| 4,082,717 | 4/1978 | Brennan et al. | 260/345.9 |
| 4,147,705 | 4/1979 | Brennan et al. | 260/345.9 |
| 4,323,506 | 4/1982 | Brennan et al. | 260/345.8 |
| 4,387,235 | 6/1983 | Brennan et al. | 549/417 |
| 5,221,756 | 6/1993 | Fleisher et al. | 549/418 |
| 5,641,489 | 6/1997 | Fleisher | 424/195.1 |
| 5,646,312 | 7/1997 | Arsenault | 549/418 |

FOREIGN PATENT DOCUMENTS

| | | |
|---|---|---|
| 47-29365 | 6/1972 | Japan . |
| 55-057582 | 4/1980 | Japan . |
| 95/29908 | 11/1995 | WIPO . |

OTHER PUBLICATIONS

Schenck, J.R. and Spielman, M.A.; The Formation of Maltol by the Degradation of Streptomycin; Communications to the Editor, Journal American Chemical Society 67:2276–2277, 1945.

Spielmann, M.A. and Freifelder, M., A Synthesis of Maltol; Journal of American Chemical Society 69:2908–2909, 1947.

Harada, R. and Iwasaki, M.; Synthesis of Maltol and Ethylmaltol; Agric. Biol. Chem; 47(12), 2921–2922, 1983.

Shono, T. and Matsumura, Y.; Novel Syntheses of Maltol and Related Compounds; Tetrahedron Letters No. 17:1363–1364, 1976.

Weeks, P.D., et al; Conversion of Secondary Furfuryl Alcohols and Isomaltol into Maltol and Related Gamma–Pyrones; J. org. Chem. 45:1109–1113, 1980.

*Primary Examiner*—Joseph K. McKane
*Attorney, Agent, or Firm*—St. Onge Steward Johnston & Reens LLC

[57] ABSTRACT

A process for recovering γ-pyrones such as maltol and/or ethyl maltol from solutions containing other substances involves an elution chromatographic treatment using a stationary phase that separates the γ-pyrones from the other substances by means of ion exclusion, size exclusion, hydrophobic partitioning, and/or chelation. In one embodiment, a cation exchange resin such as sulfonated divinyl benzene-cross-linked polystyrene is employed, and the γ-pyrones obtained can be further purified by crystallization from water and/or other means.

20 Claims, No Drawings

RECOVERY OF γ-PYRONES

TECHNICAL FIELD OF THE INVENTION

This invention relates to improved purification processes for the recovery of maltol, ethyl maltol, and other γ-pyrones that are used as ingredients in foodstuffs, perfumes, and essences to enhance the flavor and/or aroma of a variety of food and cosmetic products.

Flavor enhancement and modification are especially important aspects of food preparation and manufacture. The addition of salt, garlic, onions, and the like to different recipes has been used by cooks to improve the taste and smell of culinary dishes for hundreds, if not thousands, of years. With the discovery that certain compounds such as monosodium glutamate exist that can enhance or improve flavor without themselves having a strong flavor came the search for other compounds having a similar action.

One such compound discovered was maltol, 3-hydroxy-2-methyl-4H-pyran-4-one, a naturally-occurring substance found in the bark of young larch trees, pine needles, chicory, wood tars and oils, and roasted malt. Maltol has a characteristic caramel-butterscotch odor and a faint, fruity-strawberry aroma in dilute solutions. When added to recipes for candies, ice cream, liqueurs, and the like, it perceptibly enhances sweetness produced by sugars. As it is naturally formed in the crust of baking bread, it also imparts a "freshly baked" odor and flavor to bread and cakes when added to recipes for baked products. Since maltol is naturally formed in the roasting of coffee and cacao, it is likewise used as an enhancer of coffee and chocolate products. It thus is a desirable ingredient as a flavoring agent for a variety of foods.

Maltol also has antioxidant properties. It has been found to prolong, for example, the storage life of coffee and roasted cereal products. This increases its attractiveness as a food additive.

Closely related structurally, ethyl maltol (3-hydroxy-2-ethyl-4H-pyran-4-one) is a similarly desirable flavor/aroma additive. It imparts a somewhat fruity bouquet when used as an added ingredient to food or cosmetic formulations, alone or in combination with maltol, and exhibits other properties analogous to maltol.

BACKGROUND OF THE INVENTION

Early commercial production of maltol at the end of the last century involved the destructive distillation of wood. Then, in 1945, Schenck and Speilman obtained maltol by alkaline hydrolysis of streptomycin salts (*J. Am. Chem. Soc.* 67: 2276). The same group of investigators reported the first synthesis of maltol two years later (Spielman, M. A., and Freifelder, M., *J. Am. Chem. Soc.* 69:2908); in the process, pyromeconic acid derived from comenic acid, a fermentation product, was alkylated. A superior modification of this preparation was developed by Tait and Miller (U.S. Pat. No. 3,130,204).

Because of the increasing commercial importance of γ-pyrones, several other syntheses were subsequently reported in the chemical and patent literature. For example, a five-step procedure employing methyl alcohol as a starting material to generate an epoxy ketone which was then refluxed with water and a Dowex™ 50 ion exchange resin to yield γ-pyrone was briefly described by Shono and Matsumura in a short paper in 1976 (*Tetrahedron Letters* 17:1363). Brennan, et al., disclosed a one-pot method for preparing γ-pyrones that same year (U.S. Pat. No. 4,082,717 and its divisionals, U.S. Pat. Nos. 4,323,506, 4,147,705, and 4,387,235). The process involved contacting 1(2-furfuryl)-1-ethanol in aqueous solution with two equivalents of a halogen oxidant at room temperature and then heating until the hydrolysis of the 4-halo-dihydropyran intermediate was substantially complete. Other γ-pyrones such as ethyl maltol were prepared in an analogous manner from appropriate alcohols.

The investigators later published another synthetic scheme employing an O-methyl derivative of isomaltol, available in a simple two-step procedure from lactose (Weeks, P. D., et al., *J. Org. Chem.*, 1980, 45:1109). Trimethoxyfurfturyl alcohol was prepared in good yield via a bromination-reduction sequence, and this intermediate was converted under hydrolysis conditions directly to maltol. The paper summarized other slightly different preparative schemes involving related series of reactions using similar starting materials and intermediates to those described above (id., page 1109).

Following either synthesis or extraction from natural sources, γ-pyrones are typically recovered by crystallization, continuous extraction and/or co-distillation. Brennan, et al., for example, suggested extraction with chloroform followed by distillation and then crystallization from methanol (Example 1, column 6, lines 23 to 27). In Jap. Pat. Pub. No. 47-29365, Takaishi, et al., suggested using a basic ion-exchange resin to separate maltol from an aqueous solution employing ion exchange. Following this step wherein maltol is bound to the resin by ionic interaction, it is released from the column by employing common regeneration methods for anion exchangers, more specifically, by using NaOH. The step is followed by chloroform extraction. Harada and Iwasaki also suggested a chloroform extraction (*Agric. Biol. Chem.* 47:2921–2922 (1983)).

Though these procedures seemed promising in benchtop tests, on a commercial scale solvent extractions tend to be expensive because of the costs of the apparatus and solvents required. At lower temperatures, maltol is only somewhat soluble in water, so that large amounts of solvents are needed to extract it from the dilute aqueous solutions obtained from synthetic preparations or natural isolates. Moreover, residual organic solvent in the products are not desirable in the manufacture of food grade ingredients.

Alternative procedures such as distillations are hampered because maltol easily volatilizes with steam. It is therefore extremely difficult to obtain by concentration of aqueous solutions such as those obtained from natural source isolations or synthetic preparations. In some procedures incorporating crystallization steps, special equipment is required, and obtaining a pure product can take hours, thus increasing processing costs.

It would be desirable to have other, more economical methods of extracting and purifying maltol and other γ-pyrones, particularly methods that do not utilize organic solvents.

SUMMARY OF THE INVENTION

It is an object of the invention to provide a new, relatively inexpensive method for recovering γ-pyrones from either impure raw materials or synthetic preparations.

It is another object of the invention to provide recovery procedures that do not require the use of organic solvents.

It is a further object of the invention to provide a process that yields γ-pyrone products having desirable odor and/or taste properties.

These and other objects of the invention are accomplished by the present invention, which provides in a preferred embodiment an essentially one-step purification of maltol and/or ethyl maltol and other γ-pyrones. The process is applicable to the purification of γ-pyrones of the formula

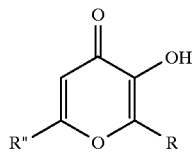

wherein R is hydrogen, an alkyl of 1 to 4 carbon atoms, phenyl or benzyl, and R" is hydrogen or an alkyl of 1 to 4 carbon atoms, such as maltol, ethyl maltol and mixtures thereof, from a solution containing other organic and inorganic substances in addition to the γ-pyrone. The solution is subjected to an elution chromatographic treatment that separates the γ-pyrones from the other substances using ion exclusion, size exclusion, hydrophobic partitioning and/or chelation. Some embodiments employ an ion exchange resin such as a cation exchange resin as the stationary phase in the treatment. A purified γ-pyrone-rich fraction is obtained, and the γ-pyrones are recovered from the fraction. In some embodiments, the γ-pyrone fraction so obtained is concentrated by evaporation, and the γ-pyrones are further purified by crystallization from water, but other purification techniques may be employed.

One embodiment illustrated below for the recovery of maltol and/or ethyl maltol from substantially aqueous solutions uses a polystyrene-based divinyl benzene cross-linked sulfonated cation exchange resin having a relatively high divinyl benzene content of about 3% to about 35%, more narrowly from about 5% to about 10%, in the sodium form, and the separation treatment is conducted at a temperature of about 0° to about 150° C., preferably from about 60° to about 100° C., and a pressure of about 0.1 to about 200, preferably from about 1 to about 10, bars. The maltol obtained can be further purified using conventional purification techniques, including crystallization from water.

DETAILED DESCRIPTION OF THE INVENTION

This invention is based upon the surprising finding that a solution containing γ-pyrones such as maltol or ethyl maltol in addition to other substances could be separated from the other substances, both organic and inorganic, using an elution chromatographic treatment which utilizes ion exclusion, size exclusion, hydrophobic partitioning, and/or chelation.

In a preferred practice of the invention, γ-pyrones, particularly maltol and ethyl maltol, are recovered from solutions containing synthetically produced γ-pyrones or from natural extracts in a simple one-step separation to yield high purity fractions. For example, synthetic or natural impure solutions having a concentration of about 10% to about 40% d.s. maltol can be purified to a purity of at least about 80%, preferably at least about 90% to 95% (or higher) using processes of the invention. As used herein, the term "d.s." is a weight percent measure of all nonaqueous substances, i.e., excluding water.

Broadly speaking, this invention provides a process for purifying a γ-pyrone of the formula

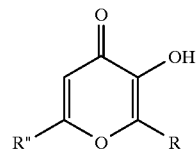

wherein R is hydrogen, an alkyl of 1 to 4 carbon atoms, phenyl or benzyl, and R" is hydrogen or an alkyl of 1 to 4 carbon atoms, in solution containing other substances in addition to the γ-pyrone by subjecting the solution to a separation that substantially purifies the γ-pyrone. By employing chromatographic separation according to the invention, it is possible to remove at least 50%, preferably 80 to 90% or more, of the impurities from γ-pyrone solutions.

As summarized above, the process is particularly adapted to the recovery of maltols wherein R" is hydrogen and R is an alkyl group as defined above, i.e., maltol, ethyl maltol, propyl maltol, butyl maltol and mixtures of these, but the process can be used with other γ-pyrones as well. It is especially advantageous for the recovery of commercially important maltol (wherein R"=hydrogen and R=a methyl group as depicted above), ethyl maltol (wherein R"=hydrogen and R=ethyl group as depicted above), and mixtures of these with each other and with other γ-pyrones. The process is useful for recovery of γ-pyrones from solutions obtained as natural product isolates, solutions from synthetic preparations of γ-pyrones, or mixtures of these.

In the practice of the invention, a solution containing γ-pyrones and other substances is subjected to an elution chromatographic treatment that separates the γ-pyrones from at least a portion of the other substances by ion exclusion, size exclusion, hydrophobic partitioning, and/or chelation. As used herein, by "solution" is meant conventional solutions containing at least one solute dissolved in a solvent, suspensions, emulsions, pseudophases, inclusion complexes, and the like fluids which can be subjected to conventional chromatographic treatment. The invention is particularly suitable for the recovery of maltol and/or ethyl maltol from substantially aqueous solutions such as those employed in maltol and/or ethyl maltol syntheses and extractions from natural sources. By "substantially" aqueous is meant at least about 50% aqueous, typically at least about 90% aqueous, in most embodiments.

In an elution chromatographic treatment according to the invention, the γ-pyrone-containing solution is typically applied to a column filled with a stationary phase which can be a resin, membrane or fiber, or combinations thereof. The stationary phase resin (membranes and/or fibers) are selected to separate the γ-pyrones in the solution by ion exclusion, size exclusion, hydrophobic partitioning, and/or chelation. The mobile phase in the treatment is typically aqueous, and organic solvents are not employed during the elution process for the preparation of food-grade γ-pyrones, though solvents may be present in the solution to be purified and may be used to regenerate the chromatographic resin in some embodiments.

The solution to be purified is generally applied to a resin-, membrane-, and/or fiber-containing column and eluted from the column using the aqueous mobile phase. The eluant may be subjected to recirculation in some embodiments. A simulated moving bed may be employed in some embodiments. Chromatographic treatments may be run in countercurrent or co-current modes.

Any stationary phase that chromatographically separates γ-pyrones from salts and other inorganic compounds as well as organic compounds using ion exclusion, size exclusion, and/or hydrophobic partitioning may be employed. Typical recovery methods of the invention involve subjecting an aqueous solution of γ-pyrones to a chromatographic separation comprising an ion exchange resin, preferably a cation exchange resin. In some embodiments illustrated hereafter, a polystyrene-based divinyl benzene (DVB) cross-linked sulfonated exchange resin is employed. The resin preferably has a relatively high DVB content of about 3% to about 35%, more narrowly from about 5% to about 10%, and is in the sodium form. Though the sodium form is often employed to enhance desalting, potassium or other cationic forms, or mixtures of cationic forms, may also be employed. One embodiment illustrated hereafter employs a resin having about 8% DVB.

Conditions for the chromatographic treatment vary with the types of stationary and mobile phases employed, the identity of the γ-pyrones to be recovered, and the solutions to be purified. The temperature for the treatment generally ranges from about 0° to about 150° C., preferably from about 60° to about 100° C., in order to produce adequate separation between salt, organic impurities and γ-pyrones without causing extensive dilution. The pressure for the treatment varies from about 0.1 to about 200, preferably from about 1 to about 10, bars.

The γ-pyrone fraction obtained from the chromatographic separation of the invention may be recycled one or more additional times through the same or a similar procedure in some embodiments, particularly where the original solution is very crude. In these or other embodiments not involving a recycling step or steps, the γ-pyrone fraction obtained from the chromatographic separation of the invention may be further purified and/or processed by ion exchange or other adsorption chromatography, filtration, activated carbon treatment, crystallization, drying, milling, and the like other preparative techniques. As mentioned above, preferred extractions are aqueous in many embodiments. As illustrated hereafter, some embodiments employ a step involving crystallization of the purified γ-pyrone from water or lower chain alcohols such as methanol, or mixtures thereof. The product obtained exhibits little color and off-flavor.

An advantage of the invention is that it provides a more economical and simpler purification for maltol, ethyl maltol, and other γ-pyrones than what is obtained by conventional continuous extraction and co-distillation processes. In preferred embodiments, the combination of ion exclusion, size exclusion, hydrophobic partitioning and chelation desalts and removes other inorganic compounds while simultaneously removing organic contaminants from γ-pyrone solutions obtained from organic syntheses or extractions from natural sources, providing a product that is at least 90 to 95% pure in preferred embodiments. As the interaction of maltol or other γ-pyrone with the stationary phase is neutral and there is no binding, elution using chemicals and/or organic solvents is not required. The product obtained from the recovery is substantially pure.

The invention has the further advantage of providing a purification procedure substantially free of organic solvents conventionally employed for maltol and ethyl maltol recoveries. In the purification of maltol or ethyl maltol according to the invention, the entire recovery procedure and any subsequent extraction or purification steps such as crystallization can be performed in an aqueous media, preferably water, lower chain alcohols such as methanol, or mixtures thereof.

EXAMPLES

The following examples are presented to further illustrate and explain the present invention and should not be taken as limiting in any regard. Unless otherwise mentioned, all percentages are by weight, and are given for the stage of processing described.

Example 1

A 2.3 m stainless steel column having an inside diameter of 20.8 cm was loaded with a sulphonated divinylbenzene cross-linked polystyrene resin (8% DVB) which was in the Na-form. The average bead size of the stationary phase was 350 μm. The column was filled with water and maintained at a temperature of 85° C. Water was then pumped through the column, and a flow rate of 63 l/h was maintained. The feed volume was 12 liters, and feed was applied into the column at a flow rate of 63 l/h. The synthetic feed solution (~17% d.s.) containing NaCl, MeOH, maltol and other organic impurities was maintained at 90° C prior to feeding into the chromatographic column. The maltol content in the feed was 4.5% d.s. (purity 27% d.s.). The effluent from the column was divided into two fractions. The first fraction contained NaCl, MeOH, and most of the organic impurities (collection started 20 liters and ended 59 liters after the beginning of the feed). The second fraction (59 to 120 l) contained maltol (>95% d.s.) and some organic impurities. The concentration of the maltol fraction was 1.0% d.s., and the yield in separation was >99%.

The maltol fraction was then concentrated up to 10% d.s. prior to crystallization from water.

Example 2

A 2.3 m stainless steel column having an inside diameter of 20.8 cm was loaded with a sulphonated divinylbenzene (8% DVB) cross-linked polystyrene resin which was in the Na-form. The average bead size of the stationary phase was 350 μm. The column was filled with water and maintained at a temperature of 85° C. Water was then pumped through the column, and a flow rate of 63 l/h was maintained. The feed volume was 8 liters, and feed was applied into the column at a flow rate of 63 l/h. A synthetic feed solution (~30% d.s.) containing NaCl, MeOH, ethyl maltol and other organic impurities was maintained at 90° C., prior to feeding into the chromatographic column. The ethyl maltol content in the feed was 5.2% d.s. (purity 26% d.s.). The effluent from the column was divided into two fractions. The first fraction contained NaCl, MeOH, and most of the organic impurities (collection started 20 liters and ended 60 liters after the beginning of the feed). The second fraction (60–145 l) contained maltol (>95% d.s.) and some organic impurities. The concentration of the ethyl maltol fraction was 0.9% d.s., and the yield in separation was >99%.

The ethyl maltol fraction was then concentrated up to 10% d.s. prior to crystallization from water.

Example 3

A 5.4 m stainless steel column having an inside diameter of 22.5 cm was loaded with a sulphonated divinylbenzene (8% DVB) cross-linked polystyrene resin which was in the Na-form. The average bead size of the stationary phase was 350 μm. The column was filled with water and maintained at a temperature of 82° C. Water was then pumped through the column, and a flow rate of 40 l/h was maintained. The feed volume was 40 liters, and feed was applied into the column at a flow rate of 47 l/h. The feed solution was a natural maltol crystallization mother liquor (~20% d.s.) containing maltol and other organic impurities such as pinene and carbohydrates. The feed solution was maintained at 95° C., prior to feeding into the chromatographic column.

The maltol content in the feed was 7.4% d.s. (purity 37% d.s.). The effluent from the column was divided into two fractions. The first fraction contained most of the organic impurities (collection started at 60 liters and ended 140 liters after the beginning of the feed). The second fraction (140 to 320 l) contained maltol (>75% d.s.) and some organic impurities. The concentration of the maltol fraction was 2.0% d.s., and the yield in separation was >99%.

Example 4

A 1.4 m glass column having an inside diameter of 9.5 cm was loaded with a sulphonated divinylbenzene cross-linked polystyrene resin which was in the Na-form. The average bead size of the stationary phase was 350 μm. The column was filled with water and maintained at a temperature of 80° C. Water was then pumped through the column, and a flow rate of 10 l/h was maintained. The feed volume was 0.5 liters, and feed was applied into the column at a flow rate of 10 l/h. The feed solution was a natural maltol extract (10% d.s.) containing maltol and other organic impurities such as pinene and carbohydrates. The feed solution was maintained at 85° C. prior to feeding into the chromatographic column. The maltol content in the feed was 1% d.s. (purity 10% d.s.). The effluent from the column was divided into two fractions. The first fraction contained most of the organic impurities (collection started at 3.5 liters and ended 10 liters after the beginning of the feed). The second fraction (10 to 16 l) contained maltol (>80% d.s.) and some organic impurities. The concentration of the maltol fraction was 0.1% d.s., and the yield in separation was >95%.

The papers and patents cited herein are expressly incorporated in their entireties by reference.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

We claim:

1. A process for purifying a γ-pyrone of the formula

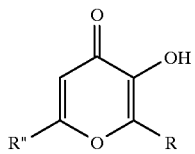

wherein R is hydrogen, an alkyl of 1 to 4 carbon atoms, phenyl or benzyl, and R" is hydrogen or an alkyl of 1 to 4 carbon atoms, in a solution containing other organic and inorganic substances in addition to the γ-pyrone comprising subjecting the solution to an elution chromatographic treatment that separates the γ-pyrones from at least a portion of the other substances by a method selected from the group consisting of ion exclusion, size exclusion, hydrophobic partitioning, chelation, and combinations thereof.

2. A process according to claim 1 wherein the chromatographic treatment comprises a combination of ion exclusion and size exclusion.

3. A process according to claim 1 wherein the chromatographic treatment comprises a combination of ion exclusion and hydrophobic partitioning.

4. A process according to claim 1 wherein the chromatographic treatment comprises a combination of size exclusion and hydrophobic partitioning.

5. A process according to claim 1 wherein the chromatographic treatment comprises a combination of ion exclusion, size exclusion, and hydrophobic partitioning.

6. A process according to claim 1 wherein the chromatographic treatment employs a cation exchange resin as the stationary phase.

7. A process according to claim 6 wherein the cation exchange resin comprises a sulfonated divinyl benzene cross-linked polystyrene.

8. A process according to claim 7 wherein the resin comprises from about 3% to about 35% divinyl benzene.

9. A process according to claim 8 wherein the resin comprises from about 5 to about 10% divinyl benzene.

10. A process according to claim 7 which is carried out at a temperature of about 0° to about 150° C. and a pressure of about 0.1 to about 200 bars.

11. A process according to claim 10 which is carried out at a temperature of about 60° to 100° C. and a pressure of about 1 to about 10 bars.

12. A process according to claim 1 wherein the γ-pyrones are selected from the group consisting of maltol, ethyl maltol, and mixtures thereof.

13. A process according to claim 12 wherein the γ-pyrones obtained are extracted after treatment by evaporation and crystallization from water.

14. A process for purifying a γ-pyrone of the formula

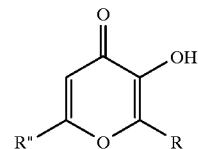

wherein R is hydrogen, an alkyl of 1 to 4 carbon atoms, phenyl or benzyl, and R" is hydrogen or an alkyl of 1 to 4 carbon atoms,
in a substantially aqueous solution containing other organic and inorganic substances in addition to the γ-pyrone comprising subjecting the solution to an elution chromatographic treatment using a stationary phase that separates the pyrones from at least a portion of the other substances simultaneously using ion exclusion, size exclusion and hydrophobic partitioning.

15. A process according to claim 14 wherein R is H and R" is an alkyl group.

16. A process according to claim 14 wherein the stationary phase comprises a cation exchange resin.

17. A process according to claim 16 wherein the cation exchange resin comprises a sulfonated divinyl benzene cross-linked polystyrene containing from about 3% to about 35 % divinyl benzene and the treatment is carried out at a temperature of about 0° to about 150° C. and a pressure of about 0.1 to about 200 bars.

18. A process according to claim 17 wherein the treatment is carried out at a temperature of about 60° to about 150° C. and a pressure of about 1 to about 10 bars.

19. A process for purifying a γ-pyrone selected from the group consisting of maltol, ethyl maltol, and mixtures thereof, in a substantially aqueous solution containing other organic and inorganic substances in addition to the γ-pyrone comprising subjecting the solution to an elution chromatographic treatment using a stationary phase that separates the pyrones from at least a portion of the other substances simultaneously using ion exclusion, size exclusion and hydrophobic partitioning, wherein the stationary phase is a cation exchange resin comprising a sulfonated divinyl benzene cross-linked polystyrene in the sodium form which contains from about 3% to about 35% divinyl benzene in the sodium form, and the treatment is carried out at a temperature of about 0° to about 150° C. and a pressure of about 0.1 to about 200 bars.

20. A process according to claim 19 wherein the resin contains from about 5% to about 10% divinyl benzene and the treatment is carried out at a temperature of about 60° C. to about 100° C. and a pressure of about 1 to about 10 bars.

* * * * *